United States Patent
Neuss et al.

(10) Patent No.: US 6,355,052 B1
(45) Date of Patent: Mar. 12, 2002

(54) DEVICE FOR CLOSURE OF BODY DEFECT OPENINGS

(75) Inventors: Malte Neuss; Franz Freudenthal, both of Bonn (DE)

(73) Assignee: pfm Produkte fur die Medizin Aktiengesellschaft, Cologne (DE)

(*) Notice: Subject to any disclaimer, the term of this patent is extended or adjusted under 35 U.S.C. 154(b) by 0 days.

(21) Appl. No.: 09/117,962

(22) PCT Filed: Feb. 4, 1997

(86) PCT No.: PCT/EP97/00500

§ 371 Date: Dec. 16, 1998

§ 102(e) Date: Dec. 16, 1998

(87) PCT Pub. No.: WO97/28744

PCT Pub. Date: Aug. 14, 1997

(30) Foreign Application Priority Data

Feb. 9, 1996 (DE) .......................................... 196 04 817

(51) Int. Cl.[7] .............................................. H61B 17/08
(52) U.S. Cl. ....................................................... 606/213
(58) Field of Search ................................ 606/213, 151, 606/215, 232, 220

(56) References Cited

U.S. PATENT DOCUMENTS

| 5,108,420 A | 4/1992 | Marks |
| 5,192,301 A | 3/1993 | Kamiya et al. |
| 5,234,458 A | 8/1993 | Metais |

(List continued on next page.)

FOREIGN PATENT DOCUMENTS

| DE | 28 22 603 | 11/1979 |
| DE | 41 04 702 | 8/1992 |
| DE | 42 22 291 | 1/1994 |
| DE | 44 10 256 | 9/1994 |
| EP | 0 474 887 | 3/1992 |
| EP | 0 545 091 | 6/1993 |
| GB | 1 509 023 | 4/1978 |
| WO | WO 93/13712 | 7/1993 |
| WO | WO 95/27448 | 10/1995 |
| WO | WO 96/01591 | 1/1996 |

OTHER PUBLICATIONS

Noel L. Mills et al., "Nonperative Closure of Left–to–Right Shunts," The Journal of Thoracic and Cardiovascular Surgery, 1976, pp. 371–378, vol. 72.

William J. Rashkind et al., "Nonsurgical Closure of Patent Ductus Ateriosus: Clinical Application of the Rashkind PDA Occluder System," Circulation, 1987, pp. 583–592, vol. 75.

James E. Lock et al., "Transcatheter Closure of Artial Septal Defects," Circulation, 1989, pp. 1091–1099, vol. 79.

E.B. Sideris et al., "Transvenous Atrial Septal Defect Occlusion in Piglets with a 'Buttoned' Double–Disk Device," Circulation, 1990, pp. 312–318, vol. 81.

Dusan Pavcnik et al., "Monodisk: Device for Percutaneous Transcatheter Closure of Cardiac Septal Defects," Cardio Vascular and Interventional Radiology, 1993, pp. 308–312, vol. 16.

(List continued on next page.)

Primary Examiner—Olik Chaudhuri
Assistant Examiner—(Vikki) Hoa B. Trinh
(74) Attorney, Agent, or Firm—Paul A. Beck & Associates

(57) ABSTRACT

The invention relates to a device for closure of defect openings in the human or animal body, which device, in a first state, can assume an elongate shape with a high ratio of length to transverse extent, and, in the implanted state, has a shape with a lower ratio of length to transverse extent, the device being deformable in the radial direction and comprising first arrangements with which the device, in the implanted state, supports itself elastically against the margin of the opening which is to be closed and thereby centers itself approximately within the opening. The device includes second arrangements which, in the implanted state, bear with positive engagement on opposite sides of the tissue surrounding the opening which is to be closed.

41 Claims, 10 Drawing Sheets

U.S. PATENT DOCUMENTS

| | | | |
|---|---|---|---|
| 5,334,217 A | | 8/1994 | Das |
| 5,425,744 A | | 6/1995 | Fagan et al. |
| 5,433,727 A | | 7/1995 | Sideris |
| 5,486,193 A | | 1/1996 | Bourne et al. |
| 5,536,274 A | | 7/1996 | Neuss |
| 5,709,707 A | * | 1/1998 | Lock et al. ................. 606/213 |

OTHER PUBLICATIONS

Gladwin S. Das et al., "Experimental Atrial Septal Defect Closure with a New, Transcatheter, Self–Centering Device," Circulation, 1993, pp. 1754–1764, vol. 88.

Eleftherios B. Sideris et al., "Occlusion of Large Atrial Septal Defects with a Centering Buttoned Device: Early Clinical Experience," American Heart Journal, 1996, pp. 356–359, vol. 131.

Christopher H. Pozza et al., "Transcatheter Occlusion of Patent Ductus Ateriosus Using a Newly Developed Self–Expanding Device," Invegative Radiology, 1995, pp. 104–109, vol. 30.

European Patent Office, "International Search Report from International Application Published Under the Patent Cooperation Treaty," International Application No.: PCT/EP97/00500.

German Patent Office, "List of References Cited in DE 196 04 817," Published: Aug. 14, 1997.

European Patent Office, International Preliminary Examination Report from International Application Published Under the Patent Cooperation Treaty, International Application No.: PCT/EP97/00500.

* cited by examiner

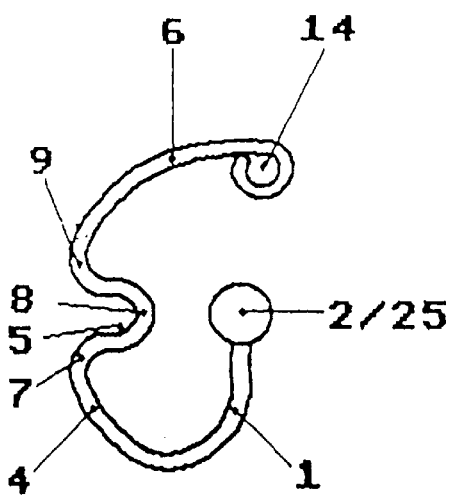
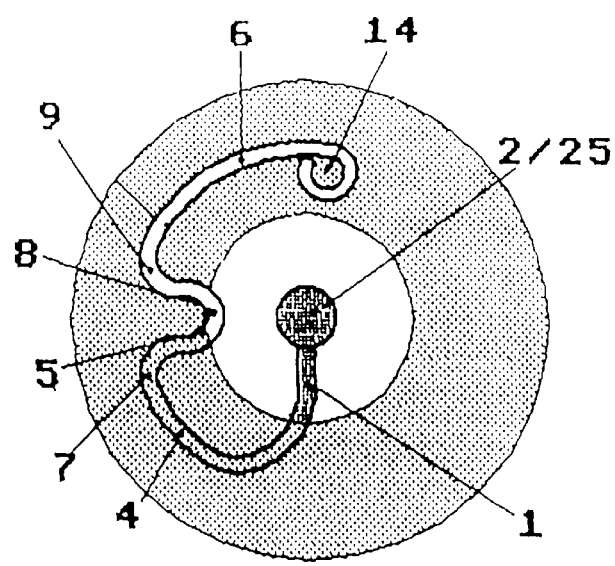
Fig. 11a         Fig. 11b
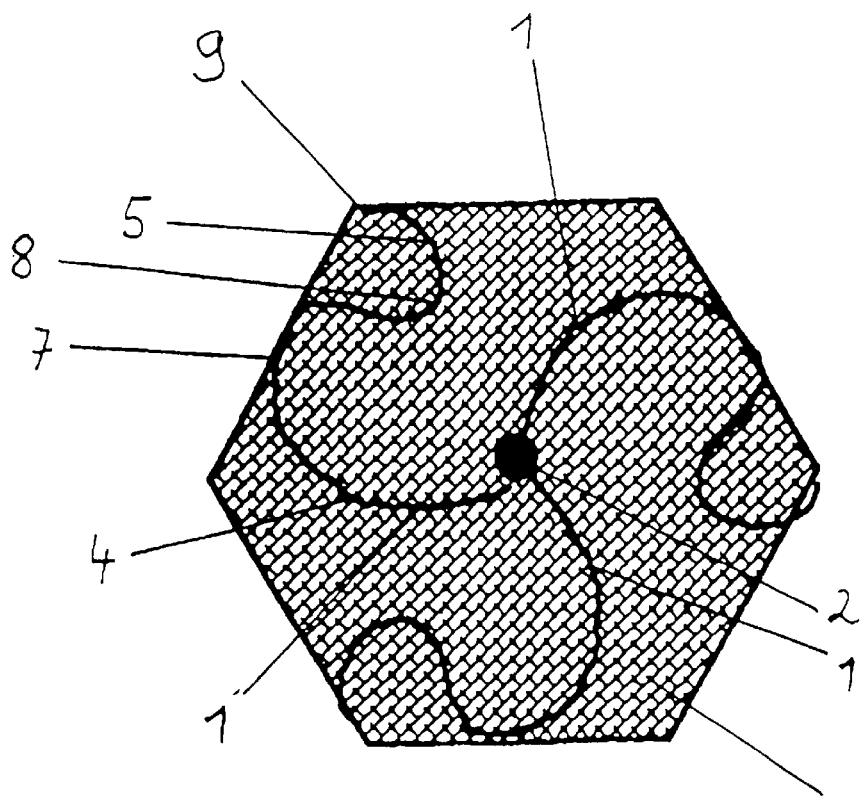
Fig. 11c

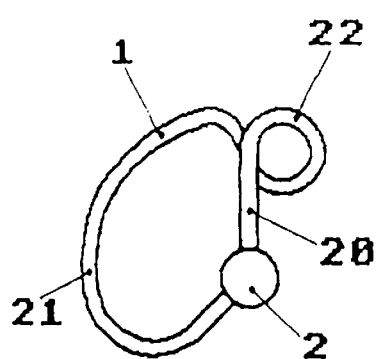
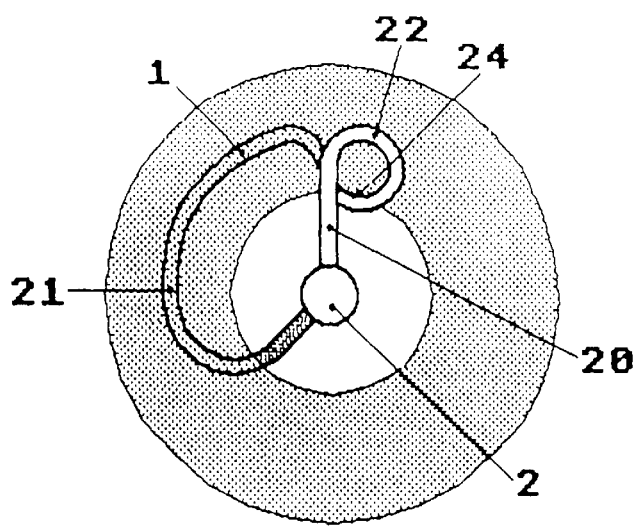
Fig. 13a    Fig. 13b
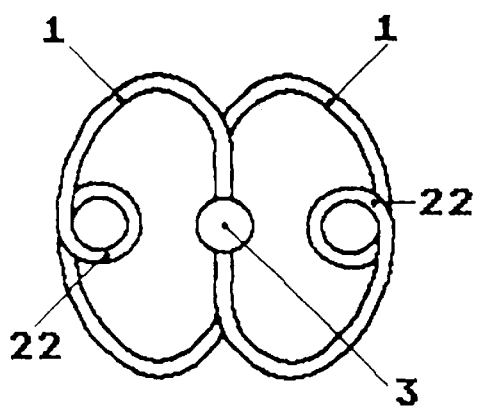
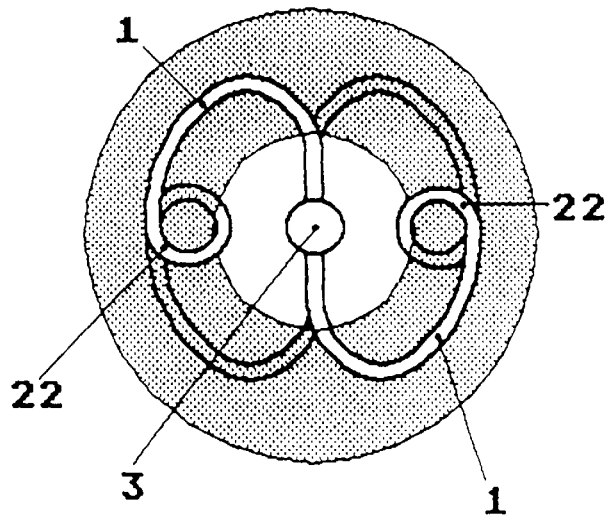
Fig. 14a    Fig. 14b

DEVICE FOR CLOSURE OF BODY DEFECT OPENINGS

BACKGROUND OF THE INVENTION

The present invention relates to a device for closure of defect openings in the human or animal body. It can be employed, for example, in the treatment of congenital heart defects with left-to-right shunt, for instance an atrial septal defect, by means of catheter techniques.

In the case of vessels to which surgical access is difficult, attempts have for many years been made to close these vessels with the aid of catheter techniques by way of the vessel pathway. A catheter intervention is less onerous on the patient than an operation, and in some cases sedation is sufficient.

Septal defects of the heart can also be closed by means of catheter techniques. The first transcatheter closures of atrial septal defects were performed in 1976 by King and Mills (Kills N. L., King T. D.: Nonoperative Closure of Left-to-right Shunts; J. Thorac. Cardiovasc. Surg. 72: 371–378, 1976) in animal experiments and on humans. The closure device used, and a subsequent device which was developed by Rashkind (Rashkind W. J., Mullins C. E., Hellenbrand W. E., et al: Nonsurgical Closure of Patent Ductus Arteriosus: Clinical Application of the Rashkind PDA Occluder System; Circulation 75: 583–592, 1987), never gained wide-spread clinical application, on account of the size of the introducing sheath of at first 23 F in the case of the first-mentioned device, and on account of the fixing hooks in the insertion device according to Rashkind. The hooks made correct centring and implantation difficult.

Two further closure devices are the so-called "clamshell device" according to Lock (Lock J. E., Rome J. J., Davis R., et al: Transcatheter Closure of Atrial Septal Defects, Experimental Studies, Circulation 79: 1091–1099, 1989) and the "buttoned device" according to Sideris (Sideris E. B., Sideris S. E., Fowlkes J. P., et al: Transvenous Atrial Septal Defect Occlusion in Piglets with a "Buttoned" Double-disk Device; Circulation 81: 312–318, 1990) which essentially have an umbrella-like form with metal struts extending outwards from the centre and acting as a support for a material covering. The left atrial umbrella and a counter-support in the right atrium are connected to one another at a central node or "button". Problems with the "clamshell device" include spontaneous embolization of the device, residual shunts and wire breaks. The disadvantages of the "buttoned devices" are an uncomfortable implantation technique, residual defects and embolizations.

D. Pavcnik et al. describe, in Cardiovasc. Intervent. Radiol. (1993) 16:308–312, an insertion device consisting of a spring-like wire coil made of special steel and covered with two layers of nylon mesh. Three sections of a hollow spiral coil are sewn as an anchoring means on the rear of the disc. Three strands of nylon monofilament yarn are looped through the anchor wires and guided through the catheter lumen. In this way the device is fixed in a reversible manner on the advance catheter. For implantation, the device is compressed and is transported through a catheter to the septal defect. The self-expanding disc opens out in the left atrium when it leaves the sheath. The anchor wires on the rear are brought into position on the right side of the atrial septum, the nylon filaments are cut through, whereupon the flexible wires spring back and press against the septal wall, so that the disc is anchored in the defect. A disadvantage of this insertion device is that the disc leaves the implantation catheter laterally and has to be turned, only with some difficulty, through 90° in the left atrium.

In Circulation Volume 88, No. 4, Part 1, October 1993, G. S. Das describes a further device for closure of atrial septal defects of the heart. It consists of two square frames of superelastic nitinol wire which are offset through 45° in relation to each other. The wire stretching across one square frame is shaped into flexible eyelets at the corners of the frame and at the midpoints of the sides. The eight eyelets in each frame make it possible for the frame to be folded up in order to introduce it into the implantation catheter. Both wire frames are covered with an elastic Dacron (polyester) fabric in each case, and these fabrics are sewn together and so form two connected discs. Each square frame can be collapsed by being folded such that the four corner eyelets are moved towards one another. The radial tensioning of the superelastic nitinol wire frames and the taut fabric have the effect that the discs lie closely opposite one another. A disadvantage of this double umbrella is that it requires a catheter diameter of at least 12 F, and, at the same time, in each case eight wire sections of the frame of a folded individual umbrella have to be transported through the catheter. Moreover, in the case of this double umbrella, a repositioning mechanism can only be attached laterally on the outside, and not in the centre, which would be more favourable for exact implantation. In addition, the umbrella shape is restricted to the square configuration, which can lead to disturbances with valve structures. In addition, after it has left the implantation catheter, the second umbrella opens out so suddenly that damage to the septum is possible.

U.S. Pat. No. Specification 5,108,420 discloses a device for closure of defect openings which, in a first state, when it is located in an insertion catheter, assumes an elongate shape and, after implantation, opens out into a second shape on account of the resiliency of the material. The device consists of a wire framework which, in a preferred embodiment, in made up of three point-symmetrical individual elements which form a common axis which, in the implanted state, extends through the opening which is to be closed. On both sides of the opening which is to be closed, these individual elements form circular arc segments which complement each other to give approximately a full circle and can be covered with a fabric. The individual elements are in this case prestressed in such a way that, in the implanted state of the device, the tissue surrounding the opening is clamped between opposite circular arc segments and the covering bears on the tissue surrounding the opening. The device is hold in position as a result of this clamping action. However, the common axis of the individual elements, and thus the device, remains movable within the opening which is to be closed. This has a number of disadvantages. On the one hand, after implantation has been performed, the device can be displaced in the radial direction in relation to the opening. For safety reasons, in order to preclude the possibility of a residual shunt, a large radius of the circular arc segments therefore has to be chosen. However, this device can then only be used on defects in which there in a sufficiently large residual tissue surface surrounding the opening. In addition, the device has to be adapted very exactly to the shape and size of the defect which is to be closed. Finally, the device has to be positioned very precisely by the operating surgeon upon implantation, which makes the intervention more difficult and also much longer.

A prosthesis for closure of an atrial or a ventricular septal defect is known from DE-A 4,222,291, which prosthesis has two units made of a resilient material and comprising six arms which extend in a radial direction, are arranged at uniform angular spacings from one another, and are connected to one another via a tension spring. In the transport state of the prosthesis, i.e. when the latter is located in the inside of a catheter, the prosthesis is stretched in the axial direction counter to the action of the tension spring, the arms of the two units being curved in the direction of the longitudinal axis. In the implanted state, the prosthesis opens out, with the two units moving towards one another on account of the spring action, and the arms being spread. The tissue surrounding the defect opening is thus clamped between the arms of the two units, as a result of which the prosthesis is held in position. This prosthesis therefore has the same disadvantages as the device according to U.S. Pat. No. Specification 5,108,420.

A device for closure of an atrial septal defect is described in DE-A 2,822,603, in which a plurality of springs made of stainless steel are arranged in pairs and are connected to each other via a hinge and so together form scissor-like support mozers for a tissue-like synthetic skin. One of the two springs paired with each other is connected to the guide catheter, and the respective other spring is connected to a probe which is movable inside the guide catheter. If the two connection sites are moved towards each other by means of relative movement of catheter and probe, the device converts from an elongate transport state to the implanted state, as a result of which the ends of the paired springs are moved towards one another in the manner of scissors and the tissue surrounding the defect is clamped. In the implanted state, this device too is movable in the radial direction within the opening which is to be closed, and this leads to the problems which have already been mentioned in connection with the device known from U.S. Pat. No. Specification 5,108,420.

A device for closure of organ passages, for example a PDA (patent ductus arteriosus), is disclosed in WO 96/01591. This device is made from a cylinder-shaped fabric comprising a memory metal alloy. It has a bell-shaped part which at one end merges into a conical end-piece of increased diameter compared to the bell-shaped part. In the transport state, e.g. within an insertion catheter, the device is elongate, and after release in the implanted state it returns to the original geometry on account of the memory effect of the metal alloy used, the bell-shaped part coming to lie inside the duct and the conical end-piece coming to lie in one of the two blood streams. The fact that the diameter of the conical part is greater than that of the duct which is to be closed prevents the device from being dislodged by the blood flow. Because of its stopper-like geometry, this device is not suitable for closure of planar defects, e.g. an atrial septal defect.

The use of a cylindrical wire fabric for the manufacture of this device has in particular the disadvantage that the individual wires of the fabric can only be moved slightly in relation to one another, and the device cannot therefore adapt to different defect geometries. The device therefore has to be adapted very precisely to the geometry of the defect which is to be closed. It is of particular disadvantage that when a cylindrical wire fabric is used, the resulting device by necessity has a circular cross-section, so that in the case of closure of oval defect openings, for example, as occur frequently in an atrial septal defect, a residual shunt remains.

An object of the present invention is to make available a device for closure of, in particular, planar defect openings in the human or animal body, which device does not have the disadvantages of the abovementioned devices.

SUMMARY OF THE INVENTION

The object is achieved by a device for closure of defect openings in the human or animal body, which device, in a first state, can assume an elongate shape with a high ratio of length to transverse extent, and, in the implanted state, has a shape with a lower ratio of length to transverse extent, the device being deformable in the radial direction and comprising first means with which the device, in the implanted state, supports itself elastically against the margin of the opening which is to be closed and thereby centres itself approximately within the opening, and the device comprises second means which, in the implanted state, bear with positive engagement on opposite sides of the tissue surrounding the opening which is to be closed, and preferably clamp this tissue.

This ensures that the device can be implanted easily and quickly and can no longer be displaced within the opening after implantation. The device can therefore be used with considerable flexibility and no longer needs to be adapted so precisely to the size and geometry of the defect opening. This is of importance particularly in the closure of septal defects of the heart, since the openings here do not in general have a circular cross-section, but instead an oval cross-section.

By means of the positive engagement of the device of the present invention, in the implanted state, on opposite sides of the tissue surrounding the opening which is to be closed, a particularly secure positioning of the device and sealing of the opening in ensured.

The device in suitably made up of discrete, non-interwoven, preferably wire-like elements. Compared in particular to the device known from WO 96/01591, this has the advantage that the individual elements of the device according to the invention are movable relative to one another within wide ranges, and the device can therefore adapt to very different, in particular also irregular, geometries of the defect opening. This makes it possible to close defect openings using standard design forms of the device according to the invention which do not have to be adapted in advance to the particular requirements of each patient, and this without compromising the easy and secure positioning of the device and in particular the secure sealing of the defect opening.

A preferred embodiment of the device according to the invention is extendible along its longitudinal axis and includes at least two wire-like, elastic elements, each of these wire-like elements being shaped to form at least two curves, and the wire-like elements being connected to one another at at least one connection site, where the peak of the first curve of each wire-like element, starting from the connection site, is at a greater distance from the longitudinal axis than the bend point of the following second curve of each wire-like element, and the peaks of these first curves of each of the wire-like elements lie essentially in a first plane, the bend points of these second curves of each of the wire-like elements lie essentially in a second plane, and the ends of these second curves of each of the wire-like elements lie essentially in a third plane, which are in each case approximately perpendicular to the longitudinal axis of the device.

The device in thus prestressed such that in the implanted state, for closure of a septal defect, the device supports itself elastically against the margin of the defect opening via the bend points of these second curves, and the peaks of the first curves in the first plane and these ends of the second curves in the third plans bear with positive engagement on different sides of the tissue surrounding the opening or clamp this tissue.

When the device is in the unstressed state, the minimum distance between two points of the second curves closest to the connection site should ideally be only slightly greater than the minimum diameter of the defect which is to be closed, in order to keep the force acting on the defect margin as small as possible for the purpose of relieving the surrounding tissue. In contrast to the devices of the prior art, however, because of the self-centring of the present device, defects can also be closed with sufficient safety using devices which are too large or too small compared to the ideal case.

In a preferred embodiment, each wire element is shaped to form three curves and the wire elements are connected to one another at both ends, both connection sites lying on the longitudinal axis of the device. In this embodiment, when the device is in the extended state, the individual wire elements can be described as M-shaped three-fold curves whose bend points of the middle curve of each element meet on the longitudinal axis of the device in the extended state. This device is prestressed in such a way that upon transition from the extended state, e.g. in the implantation catheter, into the implanted state, a rotational movement takes place in which the bend points of the middle curves move radially outwards in relation to the longitudinal axis and thereby support themselves elastically on the margin of the opening which is to be closed. At the same time, the peaks of the first and third curves also move radially outwards in opposite directions, with the peaks of the third curves corresponding to the end points of the second curves. By means of this rotational movement, the three planes defined above assume a minimum spacing from one another, almost touching. This ensures both the centring support within the opening which is to be closed, as well an the positive engagement of the device on both sides of the tissue surrounding the opening.

It is particularly advantageous if the two outer curves have a greater radius than the middle curve. This embodiment has the advantage that in the extended state of the device, the outer legs of the outer curves extend flatter relative to the longitudinal axis than do the legs extending to the bend point of the middle curve. The consequence of this is that the device does not necessarily have to be opened out in the final position, as is customary in the prior art. Instead of this, the device can, for example, be folded out (partially) in a chamber of the heart and then drawn through the opening which is to be closed. On account of the more rigid legs of the middle curve, the device is automatically arrested in the correct position in the opening. The positioning can therefore be performed simply and quickly.

Moreover, the two outer curves can have an identical or different radius of curvature. With a different radius of curvature, it is possible, for example, to ensure that, on the side of the heart with the higher pressure, the device bears on a greater surface area of the tissue surrounding the opening which is to be closed.

In an alternative embodiment of the present invention, each of these wire elements has a winding and two legs connected to the latter. It is in this case preferable if each wire-like element assumes the shape of a leg spring, in which the two legs are curved in the same direction as the winding. Alternatively, however, one leg can be curved in the same direction as the winding, and the second leg curved in the opposite direction to the winding. It is particularly advantageous if the radius of the bends of the legs in greater than the radius of the winding. The windings of each of the wire-like elements can lie essentially in a plane which in perpendicular to the longitudinal axis of the device. In order to ensure easy implantation, each wire winding consists of only one turn.

The device is in this came shaped such that in the implanted state, e.g. for closure of a septal defect, the device supports itself elastically, against the margin of the defect opening which is to be closed, via the inner side of the turn of each wire-like element, at the apex of the turn facing towards the longitudinal axis of the device, and the legs of each wire-like element bear with positive engagement on opposite sides of the tissue surrounding the opening or clamp this tissue. In this way the device is fixed elastically in the defect wall with self-centring and is secured against lateral slipping, even in the case of different wall thickness. As a result of the excellent fixing of this embodiment, only a slight residual surface of tissue surrounding the opening has to be present in order to be able to securely close the defect, with the result that this embodiment can also be employed in the case of anatomically very complicated defects.

The minimum number of wire-like elements in the embodiment described thus far is two. However, any desired number of wire-like elements can be used, for example 20 or 30. Three to six elements are preferred.

The wire-like elements can be made up of wire, a wire strand, a wire coil or a tube. The wire constituting the wire-like elements can be of any resilient, medically compatible material, e.g. surgical steel with spring characteristics, or an resorbable material with spring characteristics. However, titanium/nickel alloys with shape memory, such as nitinol, are preferred. The spring effect can be achieved, for example, by heating the material which has been brought into the desired shape, and subsequent rapid cooling (quenching). The wire cross-section can be round, oval, semicircular, square or rectangular, for example, and can also vary along the length of the wire. Alternatively, a synthetic material with corresponding elastic properties can also be used, which is particularly appropriate in the case of elements which are formed from a primary tube. The wire-like elements can, if appropriate, be wound round with platinum or gold wire or can be provided with platinum or gold rings in order to enhance the X-ray contrast.

The device can be covered at least on one side, preferably on both sides, with a mesh or a foil so as to form an umbrella or double umbrella.

If the covered wire framework is viewed along the longitudinal axis of the device in the final implanted state, then, depending on the number of the wire-like elements and the size of the curves, the outer shape of the individual umbrellas in the first-described embodiment can be triangular, four-cornered (e.g. square, rectangular or diamond-shaped), polygonal, star-shaped or continuous (e.g. round, oval or semicircular) in a large number of elements. Thus, for example, four elements with front or rear curves of equal sizes can result in two square umbrellas in the final state, whereas two elements of smaller curves and two elements of greater curves lead to two rectangular or diamond-shaped umbrellas. Apart from the height of the curves of the elements, the outer shape of the umbrellas formed also depends on the distance between the elements.

For closing an atrial septal defect, the implantation catheter is advanced from the femoral vein, for example, through the right atrium and via the septal defect into the loft atrium. The umbrella is then slowly reconfigured by pushing the device forwards and pulling the implantation catheter back in the right atrium. It facilitates the implantation procedure if, as has already been described for a preferred embodiment, the radii of the two outer curves are of different sizes, so that the rear umbrella can be drawn easily through the defect in the slightly extended state, until the bend points of the middle curves snap into place in the defect. The wire sections of the larger front umbrella, standing almost parallel to the defect on the wall of the left atrium, prevent this front umbrella from sliding through upon pulling back. The implantation catheter is in this case advantageously to be provided with such a curvature that it is perpendicular to the septal wall. In this way, an incorrect positioning of the wire-like elements on the wrong side of the septum is largely avoided.

To implant the device according to one of the embodiments described above, it has to be introduced first of all into a catheter, for which purpose it has to be extended. The extension is obtained by stretching the device out at the front and rear ends. The extended device in introduced into the catheter. When the device is pushed out of the introducing catheter at the target site, the wire framework in the first-described embodiment shortens and campresses again, increasing the height of the curves of the wire-like elements, twists and forms a double disc or a double cone. The configuration of the wire-like elements in the form of an undulating two-fold or three-fold curve has the effect that the device centres itself upon closure of the defect, which represents a great advantage over the closure devices of the prior art. A further advantage of the device according to the invention is that the replacing mechanism can engage centrally in the middle at the rear end of the wire framework, and does not have to engage on an outer corner or edge of the umbrella.

A particularly preferred embodiment of the present invention is made up of wire-like elements with two or three curves which are connected to one another only on one side. At the side opposite the connection site, the device is covered with a fabric which, depending on the number of curves of the wire-like elements, is attached either at the endpoint of the second curve of each wire element or on the third curve. The result of this is that the device is completely smooth on the side with the covering, and no parts of the device protrude beyond the fabric. If, as has been described above, this device is now placed with the fabric umbrella in the left atrium, then the risk of thrombosis is hugely reduced on account of the smooth surface in the left atrium, without adversely affecting the closure properties of the device. In this way it in possible to substantially avoid undesired side effects of the implantation, such as thrombosis in the left atrium, and resulting cerebral stroke.

For more exact positioning, a repositioning arrangement can be provided at one end of the device, preferably at a connection site, the design of this repositioning arrangement conforming with the type of repositioning mechanism of the introduction aid used.

The repositioning arrangement can be, for example, in the form of a ball (in conjunction with an introduction aid which engages around this ball), if appropriate with a loop for receiving a guide wire for the so-called over-the-wire technique, so that the umbrella can be better positioned and implanted at right angles to the septal defect wall even when the catheter is not at right angles to the wall. Other possible forms of the repositioning arrangement are, for example, an eyelet, a hook, a coupling, a clamping mechanism, as in DE-A-4,104,702, a thread connection, which is divided by a knife or by thermolysis, a double thread with eyelet, a corkscrew connection, an adhesive connection and a soldered connection which can be freed by electrolysis.

At the other end of the wire framework, the wire-like elements in the corresponding embodiments are merely connected to one another, for example by a ball, a wire twist with or without eyelets, by soldering, welding, adhesion, sewing, by a thread, by a bushing, by eyelets with or without ring. If appropriate, however, a second repositioning arrangement can also be provided, such as, for example, an eyelet for receiving a guide wire for the over-the-wire technique. The device is in this case guided over a wire and can therefore be positioned more securely and, after disconnection, can be easily removed again, also by intervention. Only after a completely correct fit of the double umbrella is this guide wire rail finally removed again. The wire-like elements do not need to be connected directly to one another; there may also be an indirect connection, e.g. via the umbrella covering.

In an alternative device for closure of defect openings in the human or animal body, a wire-like element is shaped to form a closed loop with 2(n+3) curves, where n is an integer, preferably between 1 and 5, particularly preferably 1, and in each case curves having a concave curvature alternate with curves having a convex curvature.

For insertion into a catheter, the device can assume an elongate stressed form in which every second convex curve is displaced upwards in relation to an imaginary mid-plane through the released device, and the remaining convex curves are displaced downwards, and the device is extended in this translational direction. To facilitate the insertion into the catheter, the device can have an eyelet-shaped turn at each of the peaks of the curves with convex curvature. These eyelets can be replaced in part or completely by so-called "lemon tops", i.e. curves with a very small radius of curvature.

The device is in this case shaped such that in the implanted state, for closure of a septal defect, it supports itself elastically, against the margin of the defect opening, via the inner side of the concave curves, and the convex curves bear with positive engagement on the front side and rear side, in each case alternately, of the tissue surrounding the opening.

For positioning the device, an arrangement in provided at the peak of a first convex curve, and a second arrangement is advantageously also provided at the peak of a second convex curve which is at a maximum distance from the first convex curve and, in the implanted state of the device, lies on the same side relative to the septum. These two arrangements can be two hemispheres, for example, which complement each other to form a sphere in the extended state of the device, which sphere can then be enclosed by a corresponding insertion aid. Alternatively, however, these can also be two eyelets which lie congruently one upon the other in the extended state of the device, e.g. for receiving a thread loop. This permits a controlled release of the device. In the embodiment with eyelet-shaped turns, these can function as repositioning arrangement, so that additional repositioning arrangements are unnecessary.

For closure of an atrial septal defect, for example, the implantation catheter in this embodiment too is also advanced from the femoral vein, for example, through the right atrium and via the septal defect into the left atrium. The device is then slowly reconfigured in the left atrium by pushing the device forwards and pulling the implantation catheter back. In so doing, half the convex curves open out and then bear on the septum upon further pulling back of the catheter. After complete pulling back of the catheter and slow release of the device in the right atrium, the other half of the convex curves open out, so that the convex curves bear alternately on the septum on different sides. It is particularly advantageous to use, as the repositioning arrangement, eyelets through which a thread is guided for positioning or repositioning. The advantage of this is that, upon reconfiguration of the device, both convex curves on one side of the septum can be opened out one after the other in order to avoid a sudden release of the device.

In a further embodiment of the device according to the invention, the device consists of a wire-like element which is shaped to form a closed loop with at least two, preferably four, windings spaced apart from one another, preferably consisting of a wire turn. A greater number of windings is possible but makes handling of the device more difficult.

For insertion into an implantation catheter, the device can assume an elongate shape in which every second winding is displaced upwards in relation to an imaginary mid-plane through the device, and the remaining windings are displaced downwards, and the device is extended in this translational direction. Insertion into the catheter is particularly simple if eyelet-shaped turns are provided in each case approximately in the middle of the loop sections between two adjacent windings, with the diameter of the windings being greater than the diameter of the turns. These eyelet-shaped turns serve at the same time an repositioning arrangement. In the same way as in the previously described embodiment, they can be replaced by curves having a very small radius ("lemon tops"). Embodiments without the eyelet-shaped turns have additional repositioning arrangements.

In the implanted state, for closure of a septal defect, the device supports itself elastically, against the margin of the defect opening which is to be closed, via the inner side of each winding, at the apex of the winding facing the mid-point of the device, and alternating loop sections between two adjacent windings bear with positive engagement on opposite sides of the tissue surrounding the opening. This embodiment is distinguished by a very compact structure, so that it can also be used for defects having only a little surrounding tissue. It nevertheless has a very secure fit.

In these alternative embodiments, the same materials can be used an in the other embodiments.

The wire framework of the device according to the invention can be covered completely with a fabric, a mesh or a foil in the form of a double umbrella, or else only one of the umbrellas can be covered on the inside and/or outside. In addition, the complete wire framework can be embedded in foamed material. Examples of the umbrella materials are: PETP (polyethylene terephthalate, e.g. Dacron®), polyamide (e.g. nylon), PTFE (polytetrafluoroethylene, e.g. Teflon®), silk, absorbable synthetic material (e.g. polygalactin, polydiaxonone, e.g. PDS®) as fabric, microporous polyurethane foil, flexible wire mesh made of very thin steel or nitinol wire, or combinations of the said materials. Polyurethane foam and polyvinyl foam, e.g. Ivalon®, are examples of materials suitable for the foam embedding.

The covering can be secured on the wire framework by eyelets, which are arranged on the wire-like elements, and/or by sewing, winding, pressing, adhesion, welding, soldering, shrinking and dipping. If the wire framework is made up of a loosely woven wire strand, the covering can be secured simply by sewing up the loops of the strand which are formed by individual wires.

The total thickness of the wire, the wire strand, the wire coil or the tube is 0.01–0.06 mm, preferably 0.02–0.035 mm. The minimum diameter of the implantation catheter is 6F (2 mm).

The device according to the invention can be used, for example, for closure of an atrial septal defect (ASD), a ventricular septal defect (VSD), a persistent patent ductus arteriosus (PDA), or an arteriovenous malformation, where the embodiment consisting of wire-like elements connected at both ends with three-fold curves is especially suitable for closure of large PDA, VSD and arteriovenous malformations.

BRIEF DESCRIPTION OF THE DRAWINGS

The invention will now be explained on the basis of a number of illustrations.

FIGS. 11 to 13 are views of different embodiments along the longitudinal axis of the device a) in the released state and b) in the implanted state, in which only one wire-like element is shown.

FIG. 14 shows a view of the embodiment according to FIG. 12 along the longitudinal axis of the device a) in the released state and b) in the implanted state, with two wire-like elements.

DESCRIPTION OF THE PREFERRED EMBODIMENTS

Figure 1:
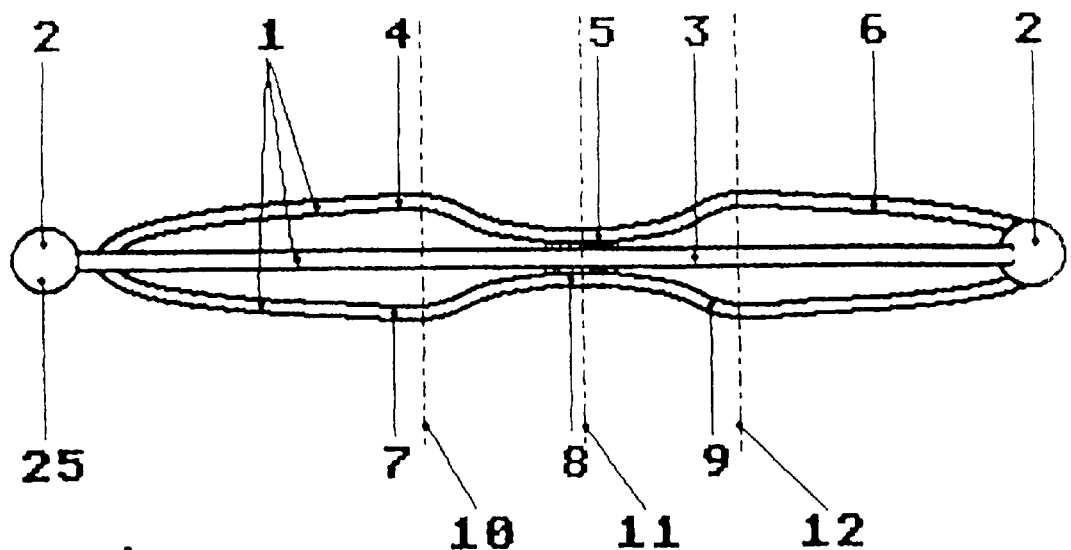
FIG. 1 is a side view of an embodiment with a wire framework consisting of four wire-like elements in the extended state.

FIG. 1 shows an embodiment of the device according to the invention comprising a wire framework consisting of four resilient, wire-like elements 1. Because of the view chosen, two elements 1 lying opposite each other are represented only as a straight line between the connection sites 2 of the elements 1. In the case of the two other elements 1, the shape of an undulating three-fold curve with two outer curves 4, 6 and one inner curve 5 can be seen. The elements 1 represented here are symmetrical, i.e. the two outer curves 4, 6 of the three-fold curve are of identical design. The elements 1 are connected to each other at their ends via ball-shaped connection sites 2. The line between the connection sites 2 corresponds to the longitudinal axis 3 of the device. One of the connection sites 2 functions as repositioning arrangement 25. In the extended state shown here, the inner curves 5 point in the direction of the longitudinal axis 3 of the device, which in this view coincides with the elements 1 represented as a straight line. It can further be seen that the points most remote from the longitudinal axis 3, i. e. the peaks 7 of the first curves 4 of each element 1, lie in a first plane 10, the points nearest the longitudinal axis, i.e. the bond points 8 of the second curves 5, lie in a second plane 11, and the endpoints 9 of the second curves 5, which coincide with the peaks of the third curves 6, of each element 1 lie in a third plane 12, which are in each case perpendicular to the longitudinal axis. FIG. 1 shows the device in the prestressed state, as is assumed by the device in the catheter, for example.

Figure 2:
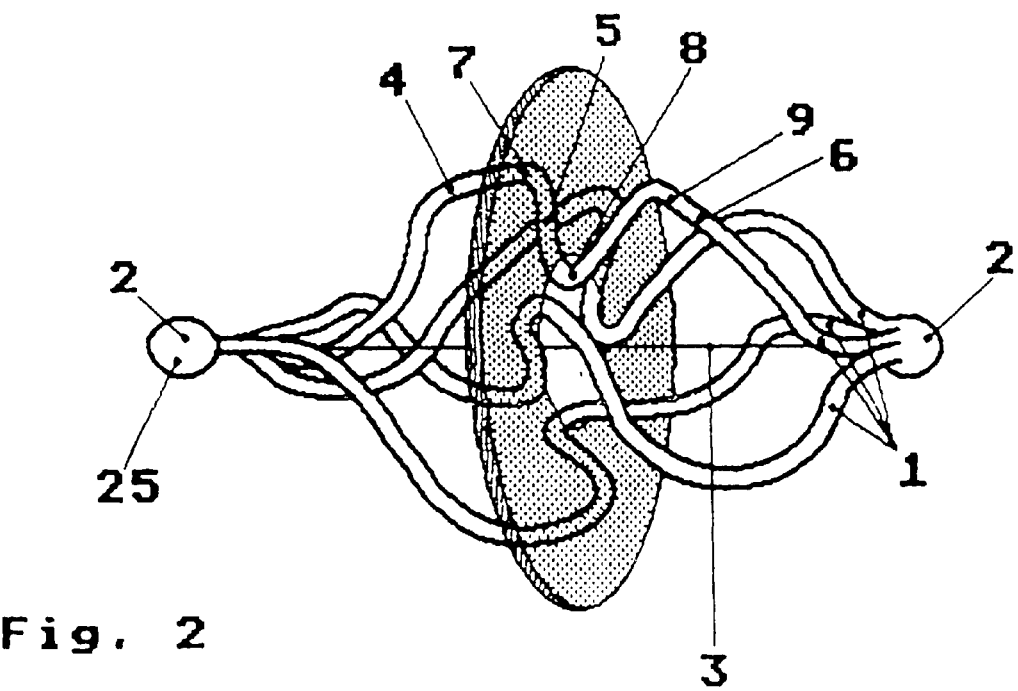
FIG. 2 is a perspective representation of the embodiment according to FIG. 1, in a prestressed state in a defect opening.

FIG. 2 also shows the device from FIG. 1 in the prestressed state on implantation in a defect opening, but here the turning about the longitudinal axis 3 has already partly begun and will continue until the final state is reached. In the perspective representation, all four wire-like elements 1 can be seen in their three-fold curve shape, and it is clear how the device is arranged and centres itself in a defect. The device supports itself elastically against the margin of the defect opening via the points 8 of the middle (second) curves 5 lying nearest to the longitudinal axis 3, i.e. via the peaks of the middle curves 5, as a result of which a more secure fit of the device in the defect and a successful closure are ensured.

Figure 3:
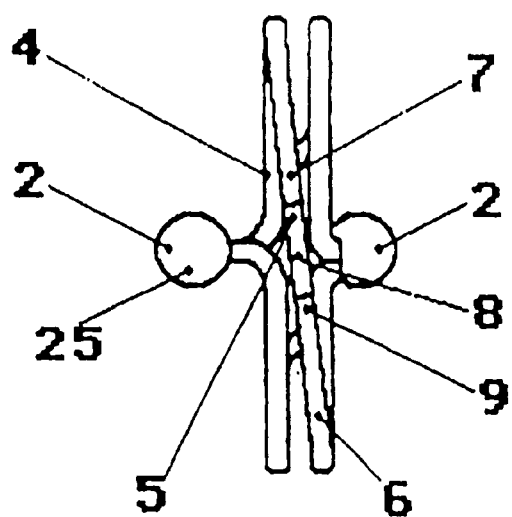
FIG. 3 in a side view of the embodiment according to FIG. 1 in the released state.

The released final state of the device can be seen in FIG. 3. For improved clarity, the defect has not been represented.

Figure 4:
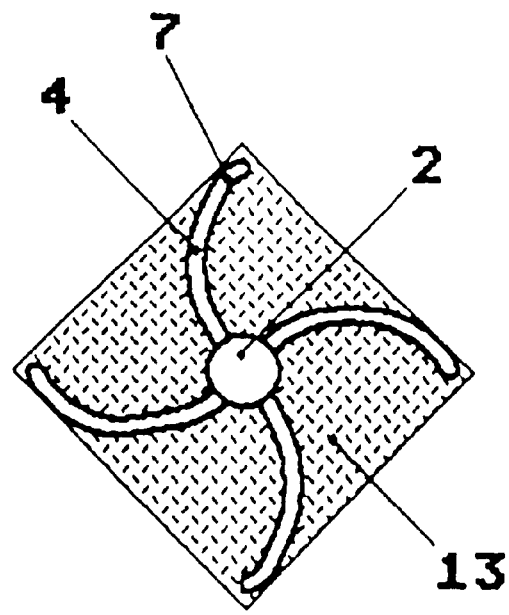
FIG. 4 in a view of the embodiment according to FIG. 1 with a square umbrella along the longitudinal axis of the device.
Figure 5A:
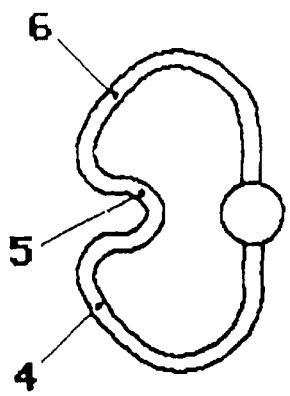
FIGS. 5 and 6 are views of the embodiment according to FIG. 1 along the longitudinal axis of the device a) in the released state and b) in the implanted state, in which only one wire-like element is shown.
Figure 5B:
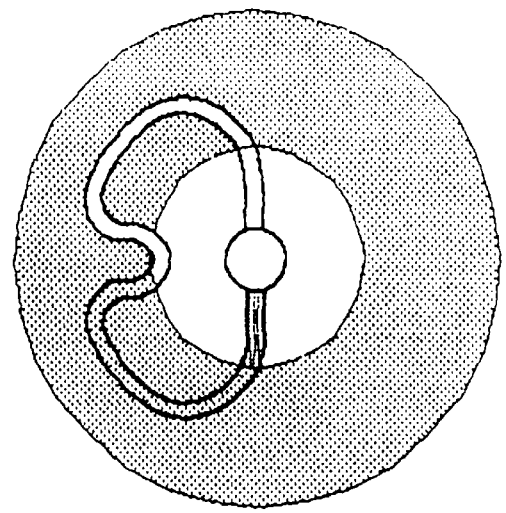
Figure 6A:
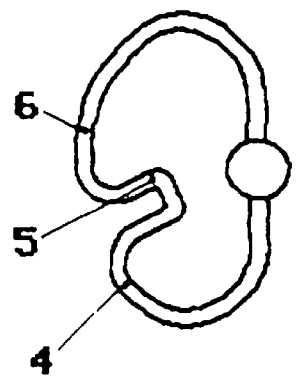
Figure 6B:
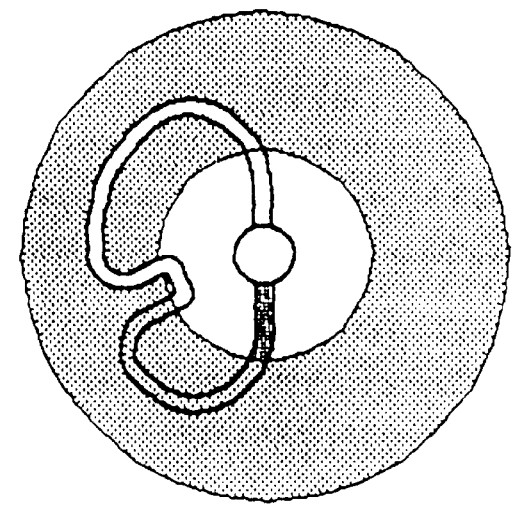

FIG. 4 is a view of a covered embodiment of the present invention along the longitudinal axis 3. A square shape of the umbrella with covering 13 can be seen, as would be obtained, for example, by covering the embodiment from FIGS. 1 and 2. The wire-like elements 1 are also at the same distance from one another, i.e. they are arranged at a 90° angle to each other about the longitudinal axis 3.

From FIGS. 5a to 6b it will be seen that the radii of the two outer curves 4, 6 in this embodiment are greater than the radius of the middle curve 5 of one element 1, while the two outer curves 4, 6 can either be the same size or of different sizes.

As can be seen from FIGS. 7 to 10, the connection site 2 designed as a ball functions as repositioning arrangement 25 on which the insertion aid 27 with repositioning function can engage.

Figure 7:
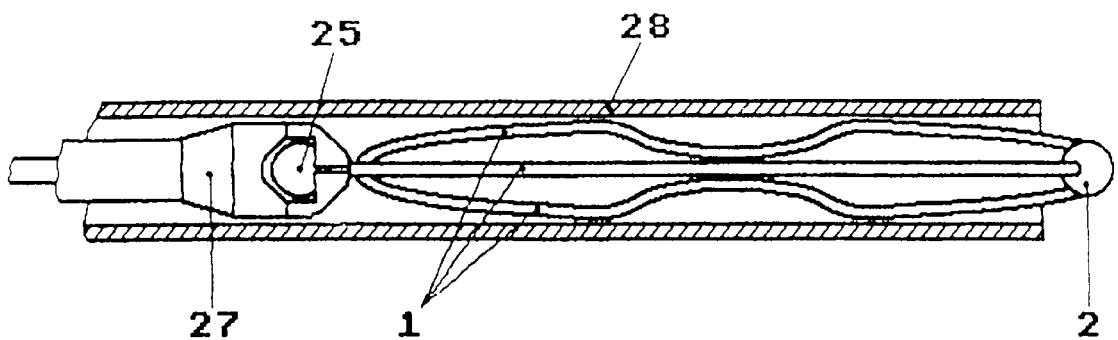
FIGS. 7 to 10 show how the shape of the embodiment according to FIG. 1 changes during insertion through a catheter and subsequent disconnection.

In FIG. 7 the device is almost completely inserted into the catheter 28, and, in the extended state, the wire framework assumes the shape of three-fold curves of low height which are connected to one another.

Figure 8:
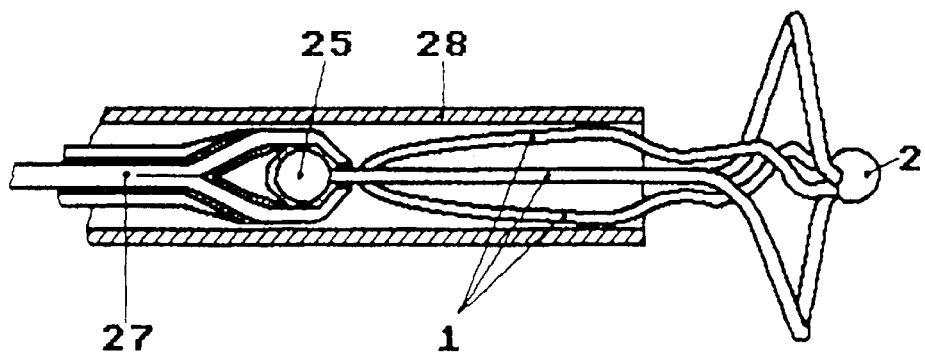

In FIG. 8 the device has already been pushed slightly further out of the catheter 28, and the rear curves 6 of the four elements 1 follow their prestressing and shorten, compress and twist.

Figure 9:
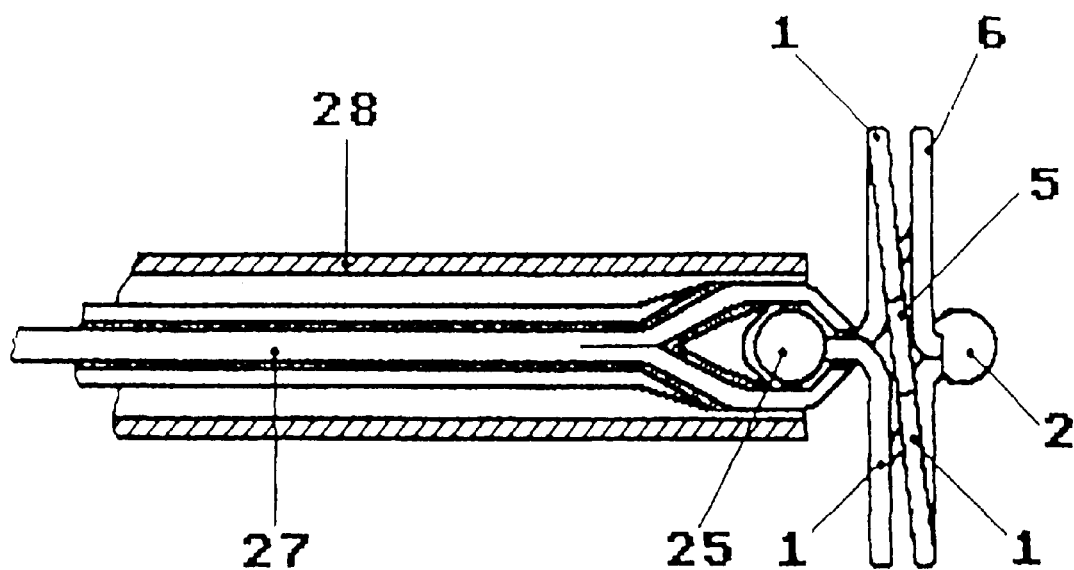

In FIG. 9 the device has been pushed so far out of the catheter 28 that the front curves 4 have also emerged from the catheter 28 and have shortened as their height increases.

Figure 10:
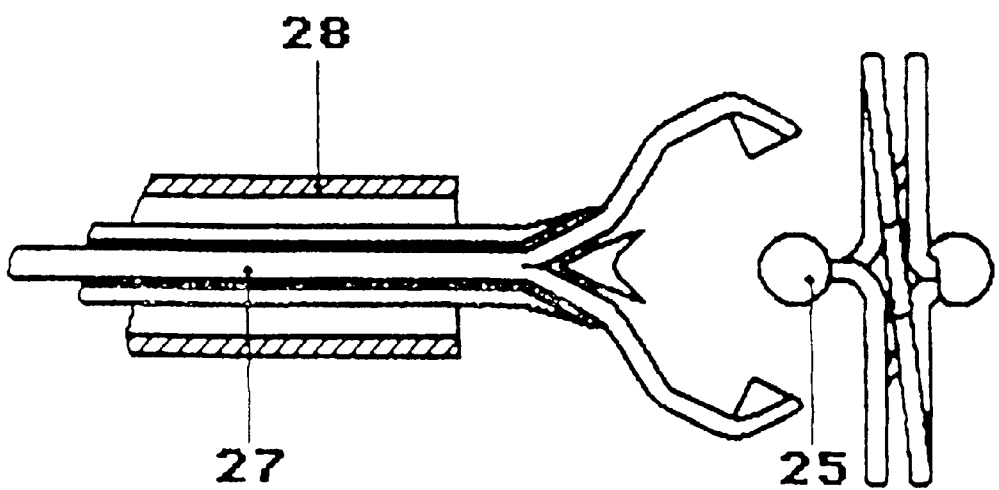

FIG. 10 shows how the device with compressed framework disconnects from the insertion aid 27 with repositioning function.

A further preferred embodiment of the device is represented in FIGS. 11a and 11b. In contrast to the embodiment in FIGS. 1 to 10, the wire-like elements 1 here are connected to one another only at one end. The arrangement of the curves remains otherwise unchanged. Since one end of the elements 1 is now free, this end is provided with an eyelet 14 in order to reduce the risk of injury. The last curve 6 can be omitted and the eyelet 14 can be arranged directly on the end 9 of the second curve 5, without thereby adversely affecting the function of the device. Alternatively, as is represented in FIG. 11c, the eyelet can be omitted, and a fabric 13 can be connected to the ends 9 of the second curves 5 of each element 1.

FIGS. 12a to 13b show two further embodiments of the device, in which the wire-like elements 1 have a winding 22 with two legs 20, 21. The winding 22 consists of a wire turn. In the embodiment according to FIG. 12, the two legs 20, 21 are curved in the same direction as the winding, the radius of curvature of the legs 20, 21 being greater than the radius of the winding 22. In the embodiment according to FIG. 13, one leg 20 is curved in the same direction as the winding 22, and the second leg 21 is curved in the opposite direction to the winding 22.

Figure 12A:
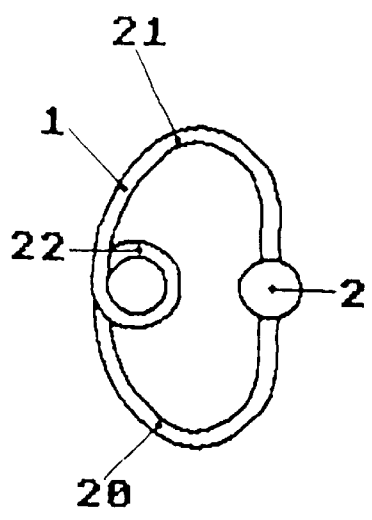
Figure 12B:
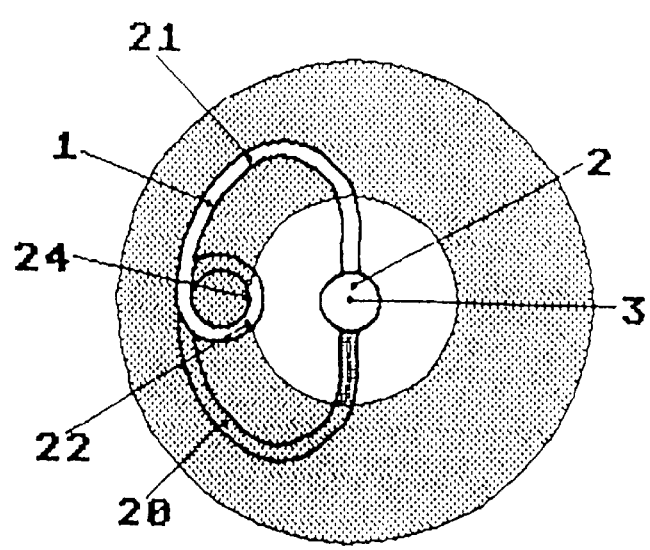

As can be seen from FIGS. 12b and 13b, the device supports itself elastically, against the margin of the opening which is to be closed, via the inner side of the winding 22, at the summit 24 of the winding 22 facing towards the longitudinal axis 3, as a result of which the self-centring of the device is achieved. The legs 20, 21 each bear with positive engagement, on opposite sides of the defect, on the tissue surrounding the opening and clamp this tissue.

In FIG. 14, the embodiment according to FIG. 12 is represented with a total of 2 wire-like elements 1. It is evident here that the windings 22 of each element lie in a plane perpendicular to the longitudinal axis 3.

Figures 15A, 15B:
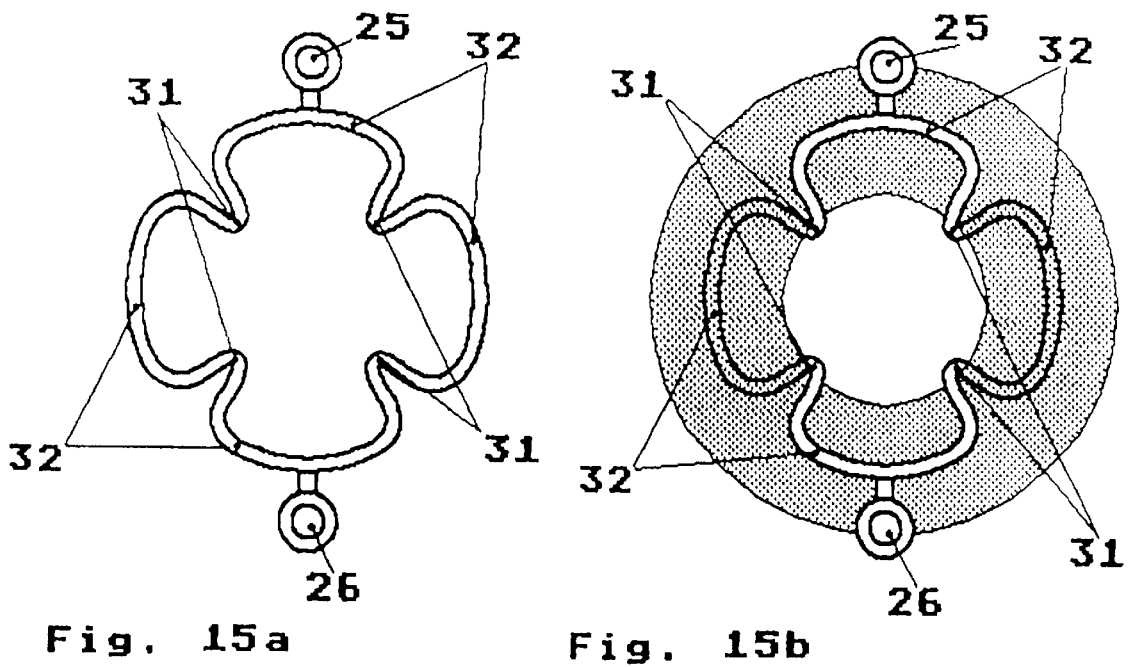
FIG. 15 shows a view of a further embodiment of the device a) in the released state and b) in the implanted state.
Figure 16:
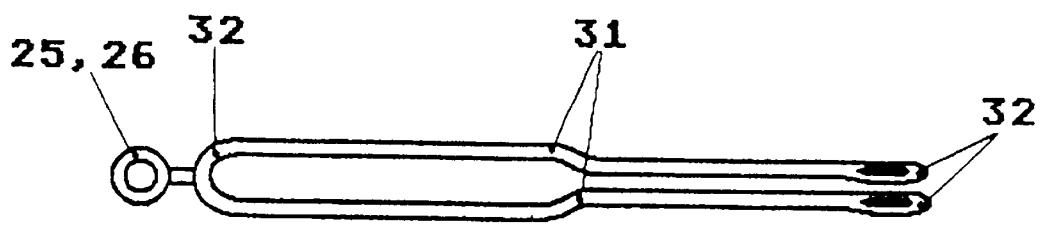
FIG. 16 is a side view of the embodiment according to FIG. 15 in the extended state.

In the embodiment represented in FIGS. 15 and 16, the device consists of a closed wire loop 1 with alternating concave curves 31 and convex curves 32. Repositioning arrangements 25, 26 are arranged in each case on two opposite convex curves 32 and lie congruently one upon the other in the extended state of the device as represented in FIG. 16. As can be seen from FIG. 15b, the device in the implanted state supports itself elastically, against the margin of the opening which is to be closed, via the bend points of the concave curves 31, while a pair of opposite convex curves 32 in each case on different sides of the defect bear with positive engagement on the tissue surrounding the opening. It is also advantageous here if the radii of the concave curves 31 are smaller than the radii of the convex curves 32.

Figure 17A:
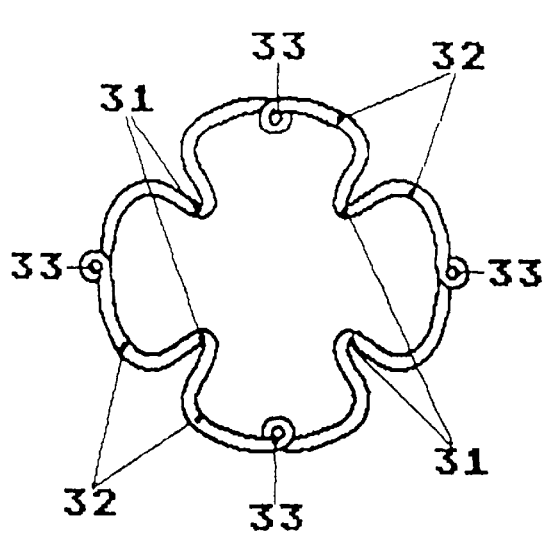
FIG. 17 shows a view of a further embodiment of the device a) in the released state and b) in the implanted state.
Figure 17B:
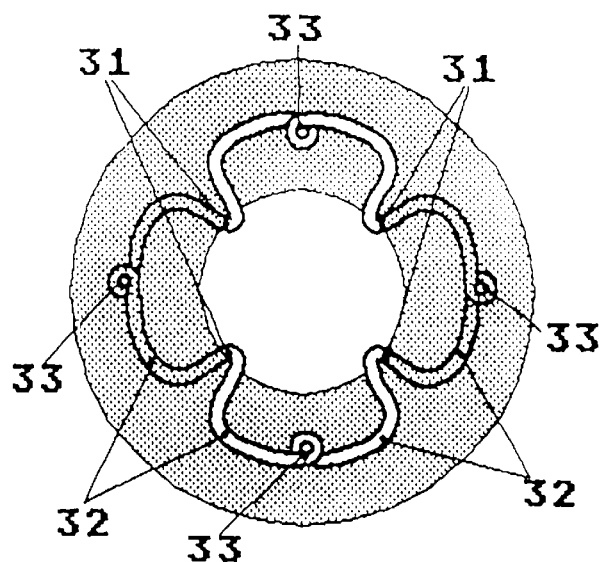

The embodiment represented in FIGS. 17a and 17b differs from the embodiment according to FIGS. 15 to 16 in that an eyelet-like turn 33 is present at the peak of each convex curve 32, which turn 33 can, on the one hand, facilitate the insertion of the device into the implantation catheter and, on the other hand, can replace the repositioning arrangement.

Figure 18A:
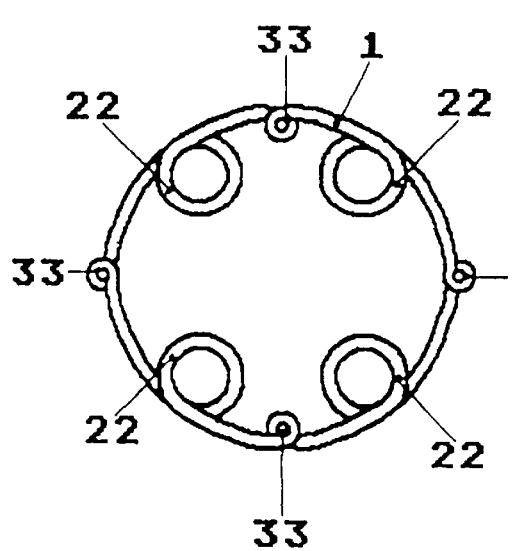
FIG. 18 shows a view of a further embodiment of the device a) in the released state and b) in the implanted state.
Figure 18B:
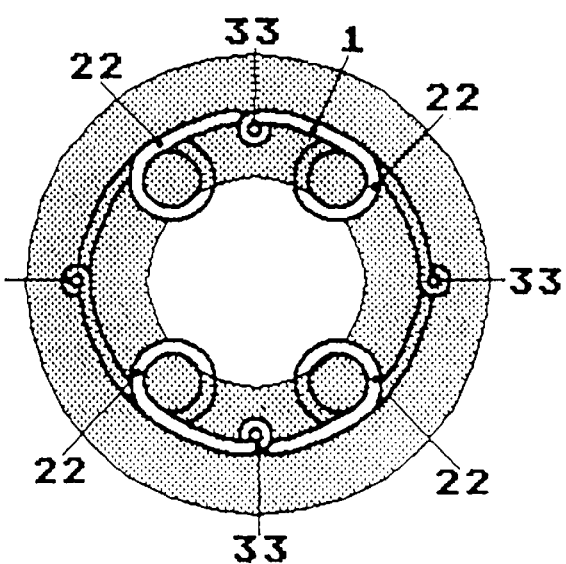

The embodiment shown in FIGS. 18a and 18b consists of a closed wire loop 1 with windings 22 and eyelet-like turns 33, and, in the same way as with the embodiment according to FIGS. 14a and 14b, the device supports itself on the margin of the defect elastically and with self-centring via the windings 22. The eyelet-like turns 33 of smaller radius have the same function as in the device according to FIGS. 17a and 17b.

What is claimed is:

1. A device for closure of defect openings in a body, comprising:

first means with which the device, in an implanted state, supports itself elastically against a margin of the opening which is to be closed and thereby centers itself approximately within the opening; and second means which, in the implanted state, bear with positive engagement on opposite sides of tissue surrounding the opening which is to be closed, wherein the device, in a first state, assumes an elongate shape with a high ratio of length to transverse extent, wherein in the implanted state the device has a shape with a lower ratio of length to transverse extent, and wherein the device is deformable and collapsible in a radial direction from the shape of its implanted state to the elongate shape of the first state by twisting the device about its axis into its collapsed state.

2. The device according to claim 1, wherein the second means clamp the tissue surrounding the opening.

3. The device according to claim 1, wherein the device includes a plurality of elements.

4. A device for closure of defect openings in a body, comprising:

at least two elastic elements, which said device is extendable along a longitudinal axis, with each of the elements shaped to form at least two curves, and with the elements being connected to one another at at least one connection site, wherein a peak of a first curve of each element, starting from the connection site, is at a greater distance from the longitudinal axis than a bend point of a following second curve of each element, wherein the peaks of the first curves of each of the elements lie substantially in a first plane, wherein the bend points of the second curves of each of the elements lie substantially in a second plane, and wherein ends of the second curves of each of the elements lie substantially in a third plane, which planes are substantially perpendicular to the longitudinal axis of the device, and wherein the device is deformable and collapsible in a radial direction from the shape of its implanted state to the elongate shape of the first state by twisting the device about its axis into its collapsed state, and wherein in an implanted state, said bend points causes said device to support itself elastically against a margin of the opening which is to be closed and thereby centers said device approximately within the opening.

5. The device according to claim 4, wherein the device is shaped such that in an implanted state for closure of a septal defect, the device supports itself elastically against a margin of the defect opening via the bend points of the second curves, and the peaks of the first curves in the first plane and the ends of the third plane bear with positive engagement on opposite sides of tissue surrounding the opening.

6. The device according to claim 5, wherein the tissue surrounding the opening is clamped between the peaks of the first curves in the first plane and the ends of the third plane.

7. The device according to claim 4, wherein the elements are configured as three curves.

8. The device according to claim 7, wherein two outer curves have a greater radius of curvature than a middle curve.

9. The device according to claim 7, wherein two outer curves have a substantially identical radius of curvature.

10. A device for closure of defect openings in a body, comprising:

at least two elastic elements connected to each other at at least one connection site, the device being extendable along a longitudinal axis, wherein each of the elements has a winding with two legs connected thereto, and wherein the device is deformable and collapsible in a radial direction from the shape of its implanted state to the elongate shape of the first state by twisting the device about its axis into its collapsed state and, wherein said elastic elements support said device elastically against a margin of a defect opening which is to be closed.

11. The device according to claim 10, wherein each element assumes the shape of a leg spring, in which the two legs are curved in the same direction as the winding.

12. The device according to claim 10, wherein one leg is curved in the same direction as the winding, and the other leg is curved in the opposite direction to the winding.

13. The device according to claim 11, wherein a radius of the bends of the legs is greater than a radius of the winding.

14. The device according to claim 10, wherein the windings of each of the elements lie substantially in a plane which is substantially perpendicular to the longitudinal axis of the device.

15. The device according to claim 10, wherein the winding of each element includes one turn.

16. The device according to claim 15, wherein the device is shaped such that in an implanted state for closure of a septal defect, the device supports itself elastically against a margin of the defect opening which is to be closed, via an inner side of a turn of each element, at an apex of the turn facing towards the longitudinal axis of the device, and the legs of each element bear with positive engagement on opposite sides of tissue surrounding the opening.

17. The device according to claim 16, wherein the tissue surrounding the opening is clamped between the legs of each element.

18. The device according to claim 7, wherein the elements are connected to one another at connection sites at both ends, and both connection sites lie on the longitudinal axis of the device.

19. A device according to claim 1, including an element which is shaped to form a closed loop with 2(n+3) curves, where n is an integer, and with curves having a concave curvature alternating with curves having a convex curvature.

20. The device according to claim 19, wherein the device assumes an elongate form in which every second convex curve is displaced upwards in relation to an imaginary mid-plane through the device, and the remaining convex curves are displaced downwards, and the device is extended in this translational direction.

21. The device according to claim 19, wherein n equals 1 to 5.

22. The device according to claim 19, wherein the element has an eyelet-shaped turn at each of the peaks of the curves with convex curvature.

23. The device according to claim 19, wherein the device is shaped such that in an implanted state for closure of a septal defect, the device supports itself elastically against a margin of the defect opening via an inner side of the concave curves, and the convex curves bear with positive engagement on a front side and a rear side, in each case alternately, of the tissue surrounding the opening.

24. A device for closure of defect openings in a body, comprising:

an element which is shaped to form a closed loop with at least two spaced apart windings, wherein eyelet-shaped turns are provided approximately in the middle of loop sections between two adjacent windings, with the diameter of the windings being greater than the diameter of the eyelet-shaped turns, and wherein the device is deformable and collapsible in a radial direction from the shape of its implanted state to the elongate shape of the first state by twisting the device about its axis into its collapsed state and, wherein said windings support said device elastically against a margin of a defect opening which is to be closed.

25. The device according to claim 24, wherein eyelet-shaped turns are provided substantially in the middle of loop sections between two adjacent windings, with the diameter of the windings being greater than the diameter of the eyelet-shaped turns.

26. The device according to claim 24, wherein the device assumes an elongate shape in which every second winding is displaced upwards in relation to an imaginary mid-plane through the device, and the remaining windings are displaced downwards, and the device is extended in this translational direction.

27. The device according to claim 24, wherein the device is shaped such that in an implanted state for closure of a septal defect, the device supports itself elastically against a margin of the defect opening which is to be closed, via an inner side of each winding, at a summit of the winding facing towards a mid-point of the device, and alternating loop sections between two adjacent windings bear with positive engagement on opposite sides of the tissue surrounding the opening.

28. The device according to claim 3, wherein the elements are made from a resilient material.

29. The device according to claim 28, wherein the elements are selected from the group consisting of wire, a wire strand, a wire coil or a tube.

30. The device according to claim 28, wherein the elements are made of wire with a round, semicircular, oval, rectangular or square cross-section.

31. The device according to claim 30 wherein the wire cross-section is variable.

32. The device according to claim 1, wherein the device is covered on at least one side with a fabric, a mesh or a foil.

33. The device according to claim 4, including an arrangement for positioning or repositioning the device.

34. The device according to claim 22, wherein the eyelet-shaped turns at the same time act as an arrangement for positioning or repositioning.

35. The device according to claim 33, wherein the arrangement for positioning or repositioning the device is arranged at one of the connection sites.

36. The device according to claim 19, wherein an arrangement for positioning or repositioning is arranged at a peak of a first convex curve.

37. The device according to claim 36, wherein a second arrangement for positioning or repositioning is arranged at a peak of a second convex curve which is at a maximum distance from the first convex curve and, in an implanted state of the device, lies on the same side relative to a septum.

38. The device according to claim 37, wherein both positioning arrangements are configured such that they are jointly grippable by a repositioning device.

39. The device according to claim 1, wherein the device has radiopaque markings.

40. The device according to claim 10, wherein the elements are connected to one another at connection sites at both ends, and both connection sites lie on the longitudinal axis of the device.

41. The device according to claim 7, wherein two outer curves have a different radius of curvature.

* * * * *

UNITED STATES PATENT AND TRADEMARK OFFICE
CERTIFICATE OF CORRECTION

PATENT NO.   : 6,355,052 B1
DATED         : March 12, 2002
INVENTOR(S)  : Malte Neuss et al.

It is certified that error appears in the above-identified patent and that said Letters Patent is hereby corrected as shown below:

<u>Column 1,</u>
Line 19, delete "Kills" and insert -- Mills --.

<u>Column 2,</u>
Line 34, delete second "in" and insert -- is --.
Line 46, delete "hold" and insert -- held --.

<u>Column 3,</u>
Line 17, delete "mozers" and insert -- members --.

<u>Column 4,</u>
Line 27, delete "in" and insert -- is --.
Line 63, delete "plans" and insert -- plane --.

<u>Column 5,</u>
Line 30, delete "an" and insert -- as --.
Line 60, delete "in" and insert -- is --.
Line 62, delete second "in" and insert -- is --.
Line 66, delete "came" and insert -- case --.

<u>Column 6,</u>
Line 59, delete "loft" and insert -- left --.

<u>Column 7,</u>
Line 13, delete "in" and insert -- is --.
Line 16, delete "campresses" and insert -- compresses --.

<u>Column 8,</u>
Line 38, delete "in" and insert -- is --.

<u>Column 9,</u>
Line 21, delete "an" and insert -- as --.
Line 39, delete "an" and insert -- as --.

UNITED STATES PATENT AND TRADEMARK OFFICE
CERTIFICATE OF CORRECTION

PATENT NO. : 6,355,052 B1
DATED : March 12, 2002
INVENTOR(S) : Malte Neuss et al.

It is certified that error appears in the above-identified patent and that said Letters Patent is hereby corrected as shown below:

Column 10,
Line 18, delete "in" and insert -- is --.
Line 20, delete "in" and insert -- is --.

Column 11,
Line 5, delete "bond" and insert -- bend --.

Signed and Sealed this

Eighth Day of April, 2003

JAMES E. ROGAN
*Director of the United States Patent and Trademark Office*